United States Patent [19]

Denzel et al.

[11] 4,091,219
[45] May 23, 1978

[54] AMINO DERVIATIVES OF 1,2,3,4-TETRAHYDRO-2-OXOPYRIDO[2,3-b]-PYRAZINE CARBOXYLIC ACIDS AND ESTERS

[75] Inventors: Theodor Denzel, Regensburg; Hans Hoehn, Tegernheim, both of Germany

[73] Assignee: E. R. Squibb & Sons, Inc., Princeton, N.J.

[21] Appl. No.: 832,146

[22] Filed: Sep. 12, 1977

Related U.S. Application Data

[62] Division of Ser. No. 769,633, Feb. 17, 1977.

[51] Int. Cl.² ............................................ C07D 471/04
[52] U.S. Cl. ........................................ 544/117; 544/58; 544/350; 544/365
[58] Field of Search ................................ 544/117, 58; 260/250 BC, 268 BC

[56] References Cited

U.S. PATENT DOCUMENTS

B 491,883  2/1976  Denzel et al. .................. 260/250 BC

*Primary Examiner*—Alan L. Rotman
*Assistant Examiner*—R. W. Ramsuer
*Attorney, Agent, or Firm*—Lawrence S. Levinson; Merle J. Smith

[57] ABSTRACT

Amino derivatives of 1,2,3,4-tetrahydro-2-oxopyrido[2,3-b]pyrazine carboxylic acid and esters and their acid addition salts which have the general formula

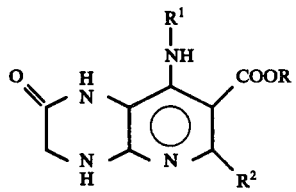

are useful as anti-inflammatory agents and central nervous system depressants.

5 Claims, No Drawings

AMINO DERIVATIVES OF 1,2,3,4-TETRAHYDRO-2-OXOPYRIDO[2,3-b]-PYRAZINE CARBOXYLIC ACIDS AND ESTERS

This is a division of application Ser. No. 769,633, filed Feb. 17, 1977.

SUMMARY OF THE INVENTION

In prior U.S. Pat. Nos. 3,935,222, Jan. 27, 1976, and 3,984,412, Oct. 5, 1976, it was found that certain tetrahydropyrazolo[3,4-b]pyridin-6-one derivatives and pyrido[2,3-b]pyrazine carboxylic acid and ester derivatives, respectively, have central nervous system and anti-inflammatory properties. It has now been found that new amino derivatives of 1,2,3,4-tetrahydro-2-oxo-pyrido[2,3-b]pyrazine-7-carboxylic acids and esters and acid addition salts thereof which have the general formula

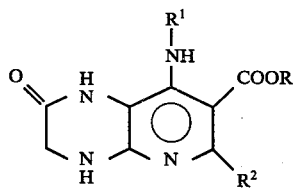

have central nervous system depressant and anti-inflammatory properties.

The symbols in the foregoing formula and throughout this specification have the following meanings.

R and $R^2$ each is hydrogen or lower alkyl.

$R^1$ is hydrogen, lower alkyl, phenyl, substituted phenyl or the lower alkyl may also bear an amino group

wherein $R^3$ and $R^4$ each is lower alkyl or $R^3$ and $R^4$ together with the nitrogen may form a heterocyclic radical like morpholino, thiamorpholino, piperazino or piperidino. In other words, $R^1$ represents the amino-lower alkylene group -lower alkylene

wherein $R^3$ and $R^4$ each is lower alkyl or combine to complete one of the heterocyclics named above, i.e., $R^1$ includes di(lower alkyl)amino-lower alkylene, morpholino-lower alkylene, thiamorpholino-lower alkylene, piperazino-lower alkylene or piperidino-lower alkylene.

The lower alkyl groups in any of the foregoing radicals include straight or branched chain hydrocarbon groups containing 1 to 7 carbon atoms. Examples of the groups contemplated are methyl, ethyl, propyl, isopropyl etc. Lower alkyl groups of 1 to 4 carbon atoms are preferred, especially the 1 and 2 carbon members of this group. The lower alkylene groups are of similar type. The substituted phenyl groups include one or two simple substituents (preferably only one substituent, but they are the same groups if disubstituted), i.e., lower alkyl, lower alkoxy, halogen (F, Cl, Br or I, preferably Cl or Br), $CF_3$, amino or carboxy. Examples of the types of groups contemplated are o-, m- or p-chlorophenyl, o-, m- or p-tolyl, 2,5-dichlorophenyl, 3,5-dimethylphenyl or 3,4-dimethoxyphenyl.

Preferred embodiments of this invention are as follows:

R is hydrogen or lower alkyl of 1 to 4 carbon atoms, especially ethyl.

$R^1$ is hydrogen, lower alkyl of 1 to 4 carbon atoms, especially butyl or methylpropyl, di(lower alkyl)amino (lower alkylene), especially dimethylaminoethyl or dimethylaminopropyl, or morpholino-lower alkylene, especially morpholinopropyl.

$R^2$ is lower alkyl, especially methyl.

DETAILED DESCRIPTION

The new compounds of formula I are formed by the following series of reactions.

A 4,6-dihydroxypyridine carboxylic acid ester of the formula

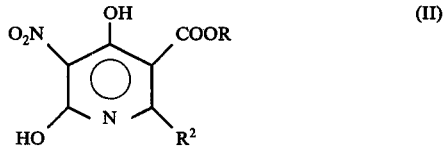

[produced analogous to the procedure described in Chem. Ber. 99, 244 (1966)] wherein R is lower alkyl, is made to react with an inorganic acid chloride like phosphorus oxychloride, producing a dichloro compound of the formula

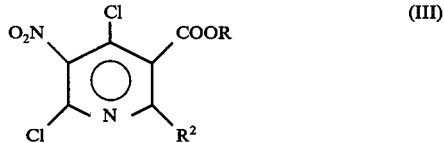

This compound is now treated with an amine $H_2NR^1$ in the presence of a base, e.g., an alkylamine like triethylamine, forming a compound of the formula

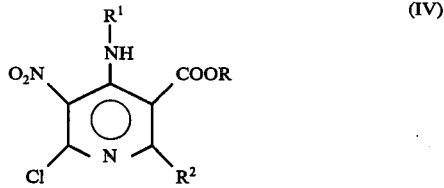

Reaction of the compound of formula IV with a glycine ester (or its salt) of the formula

         (v)

in an alcohol solvent like methanol in the presence of a base like triethylamine, preferably heating at about reflux temperature, produces a compound of the formula

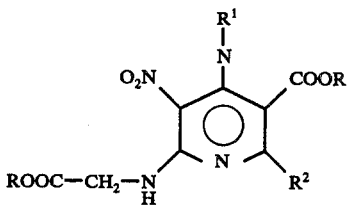

Hydrogenation of this product, e.g., catalytically in the presence of palladium-carbon, results in the formation of the compound of formula I.

The ester can be converted to the acid, i.e., wherein R is hydrogen, with a dilute alkali hydroxide like sodium hydroxide.

The bases of formula I form acid addition salts by reaction with an equivalent amount of one of the common inorganic and organic acids. Such salts include the hydrohalides, e.g., hydrobromide, hydrochloride, sulfate, nitrate, phosphate, acetate, citrate, oxalate, tartrate, maleate, succinate, benzoate, ascorbate, alkanesulfonate, e.g., methanesulfonate, arylsulfonate, e.g., benzenesulfonate, etc. It is frequently convenient to purify or isolate the product by forming an insoluble salt which is not necessarily physiologically acceptable. The base is then obtained by neutralization and another salt can then be formed by treatment with the appropriate inorganic and organic acid.

The new compounds of this invention have anti-inflammatory properties and are useful, for example, to reduce local inflammatory conditions such as those of an edematous nature or resulting from proliferation of connective tissue in various mammalian species such as rats, dogs and the like when given orally in dosages of about 10 to 50 mg/kg/day, preferably 10 to 25 mg/kg/day, in single or 2 to 4 divided doses, as indicated by the carageenan edema assay in rats. The active substance can be utilized in compositions such as tablets, capsules, solutions or suspensions containing up to about 300 mg. per unit of dosage of a compound or mixture of compounds of formula I or physiologically acceptable acid addition salt thereof. They are compounded in conventional manner with a physiologically acceptable vehicle or carrier, excipient, binder, preservative, stabilizer, flavor, etc. as called for by accepted pharmaceutical practice. Topical preparations containing about 0.01 to 3 percent by weight of active substance in a lotion, salve or cream can also be used.

The compounds of this invention are also central nervous system depressants and can be used as tranquilizers or ataractic agents for the relief of anxiety and tension states, for example, in mice, cats, rats, dogs and other mammalian species. For this purpose, a compound or mixture of compounds of formula I, or non-toxic, physiologically acceptable acid addition salt thereof, is administered orally or parenterally in a conventional dosage form such as tablet, capsule, injectable or the like. A single dose, or preferably 2 to 4 divided daily doses, provided on a basis of about 3 to 50 mg. per kg. per day, preferably about 3 to 15 mg. per kg. per day, is appropriate. A conventional dosage in oral or parenteral form is compounded by incorporating about 10 to 250 mg. per unit of dosage with conventional vehicle, excipient, binder, preservative, stabilizer, flavor or the like as called for by accepted pharmaceutical practice.

The following examples constitute preferred embodiments and also illustrate how these and other members of the group are produced. Simple variation of the reactants and substitution in the reaction sequences described below readily yield other compounds within the scope of the invention. All temperatures are in degrees celsius.

EXAMPLE 1

1,2,3,4-Tetrahydro-6-methyl-8-[(1-methylpropyl)amino]-2-oxopyrido[2,3-b]pyrazine-7-carboxylic acid, ethyl ester (a) 4,6-Dichloro-2-methyl-5-nitropyridine-3-carboxylic acid, ethyl ester 242 g. of 4,6-dihydroxy-2-methyl-5-nitropyridine-3-carboxylic acid, ethyl ester (1 Mol.) are heated at 80° with 500 ml. of phosphorus oxychloride for 60 hours. After this time, the excess phosphorus oxychloride is decomposed by pouring into ice water. The precipitate is filtered off and recrystallized from petroleum ether using charcoal, yield: 195 g. (70%); m.p. 45°–46°.

(b) 6-Chloro-2-methyl-4-(1-methylpropyl)amino-5-nitropyridine-3-carboxylic acid, ethyl ester 139.5 g. of 4,6-dichloro-2-methyl-5-nitropyridine-3-carboxylic acid, ethyl ester (0.5 Mol.) are dissolved in about 500 ml. methanol. 60 g. of triethylamine are added and the solution is heated at reflux temperature. At this point, 36.5 g. of sec. butylamine are added dropwise. After the addition is completed, heating is continued for ten minutes. The solvent is then removed in vacuo and 500 ml. of ethyl acetate are added to the residue. The triethylamine hydrochloride is filtered off and the solvent evaporated. The resulting yellow oil, 6-chloro-2-methyl-4-(1-methylpropyl)amino-5-nitropyridine-3-carboxylic acid, ethyl ester is recrystallized with methanol, yield: 107 g. (68%); m.p. 33°–35° (methanol).

(c) 6-(Ethoxycarbonylmethyl)amino-2-methyl-4-(1-methylpropyl)amino-5-nitropyridine-3-carboxylic acid, ethyl ester 18.7 g. of 6-chloro-2-methyl-4-(1-methylpropyl)-amino-5-nitropyridine-3-carboxylic acid, ethyl ester, 8.2 g. of glycine ester hydrochloride and 19 g. of triethylamine are refluxed in 200 ml. of alcohol for 4 hours. The solution is evaporated to dryness, and the residue extracted with 200 ml. of diethyl ether. The ether is removed by distillation and the residue, 6-(ethoxycarbonylmethyl)amino-2-methyl-4-(1-methylpropyl)amino-5-nitropyridine-3-carboxylic acid, ethyl ester is recrystallized from methanol, yield: 16.2 g. m.p. 43°–45°.

(d) 1,2,3,4-Tetrahydro-6-methyl-8-[(1-methylpropyl)amino]-2-oxo-pyrido[2,3-b]pyrazine-7-carboxylic acid, ethyl ester 16 g. of the product of Example 1c are dissolved in 200 ml. of butanol. About 0.1 g. of palladium on charcoal (10%) is added and the mixture is hydrogenated at 100° at ordinary pressure. After the theoretical amount of hydrogen has been absorbed, the catalyst is filtered off and the solvent removed in vacuo. The residue, 1,2,3,4-tetrahydro-6-methyl-8-[(1-methylpropyl)amino]-2-oxo-pyrido[2,3-b]-pyrazine-7-carboxylic acid, ethyl ester is recrystallized from methanol, yield: 7.2 g.; m.p. 157°–159°. Treatment with dilute sodium hydroxide solution yields 1,2,3,4-tetrahydro-6-methyl-8[(1-methylpropyl)amino]-2-oxopyrido[2,3-b]-pyrazine-7-carboxylic acid.

EXAMPLE 2

8-(Butylamino)-6-methyl-1,2,3,4-tetrahydro-2-oxopyrido[2,3-b]-pyrazine-7-carboxylic acid, ethyl ester When the sec. butylamine is replaced by n-butylamine, in part b of the procedure of Example 1, 4-butylamino-6-chloro-2-methyl-5-nitropyridine-3-carboxylic acid, ethyl ester is obtained; m.p. 33°–35° (methanol).

This compound is processed as described in Example 1c and 1d through the reaction with glycine ester, followed by the hydrogenation step. By this procedure, 8-(butylamino)-6-methyl-1,2,3,4-tetrahydro-2-oxopyrido[2,3-b]pyridine-7-carboxylic acid, ethyl ester is obtained, yield: 73%; m.p. 186°–188° (methanol).

EXAMPLE 3

8[[2-(Dimethylamino)propyl]amino]-1,2,3,4-tetrahydro-2-oxopyrido[2,3-b]pyrazine-7-carboxylic acid, ethyl ester (a)

4-[[3-(Dimethylamino)propyl]amino]-6-chloro-2-methyl-5-nitropyridine-3-carboxylic acid, ethyl ester 139 g. of 4,6-dichloro-2-methyl-5-nitropyridine-3-carboxylic acid, ethyl ester (0.5 Mol.) of Example 1a are dissolved in about 500 ml. of methanol. 60 g. of triethylamine are added and the solution is heated at reflux temperature. At this point, 50.1 g. of [3-(dimethylamino)propyl]amine are added dropwise. After the addition is completed, heating is continued for ten minutes. The solvent is removed in vacuo and the residue is suspended in 200 ml. of water. The aqueous mixture is made alkaline with 10% sodium hydroxide solution and extracted three times with 200 ml. portions of ethyl acetate. The organic layer is dried over calcium chloride, evaporated to dryness and crystallized with petroleum ether to obtain 4-[[3-(dimethylamino)propyl]amino]-6-chloro-2-methyl-5-nitropyridine-3-carboxylic acid, ethyl ester, yield: 102 g. (59%); m.p. 20°.

(b)

8-[[3-(Dimethylamino)propyl]amino]-1,2,3,4-tetrahydro-2-oxopyrido[2,3-b]pyrazine-7-carboxylic acid, ethyl ester 17.6 g. of 4-[[3-(dimethylamino)propyl]amino]-6-chloro-2-methyl-5-nitropyridine-3-carboxylic acid, ethyl ester, 7.4 g. of glycine ethyl ester, hydrochloride and 11 g. of triethylamine are refluxed together with stirring in 200 ml. of alcohol for 4 hours. After this time, the solvent is removed in vacuo and the residue treated with aqueous sodium hydroxide solution. The mixture is extracted three time with 50 ml. portions of ethyl acetate. The extracts are combined, about 0.5 g. palladium on charcoal is added and the mixture is hydrogenated at 3 atmospheres hydrogen pressure and 60°. When the theoretical amount of hydrogen is absorbed, the reaction is stopped, the catalyst filtered off and the solvent removed in vacuo. The crystalline residue, 8-[[3-(dimethylamino)propyl]amino]-1,2,3,4-tetrahydro-2-oxopyrido[2,3-b]pyrazine-7-carboxylic acid, ethyl ester is purified by recrystallization from methanol, yield: 8 g., m.p. 163°–165°.

The hydrochloride salt is formed by treating the above product with ethanolic hydrogen chloride.

EXAMPLE 4

8-[[2-(Dimethylamino)ethyl]amino]-1,2,3,4-tetrahydro-2-oxopyrido[2,3-b]pyrazine-7-carboxylic acid, ethyl ester By substituting [2-(dimethylamino)ethyl]amine for the [3-(dimethylamino)propyl]amine in the procedure of Example 3a and this compound is processed as described in Example 3a and 3b, 8-[[2-(dimethylamino)ethyl]amino]-1,2,3,4-tetrahydro-2-oxopyrido[2,3-b]pyrazine-7-carboxylic acid, ethyl ester is obtained, m.p. 183°–185° (methanol).

EXAMPLE 5

1,2,3,4-Tetrahydro-6-methyl-8-[[3-(4-morpholinyl)-propyl]amino]-2-oxopyrido[2,3-b]pyrazine-7-carboxylic acid, ethyl ester When the [3-(dimethylamino)propyl]amine is replaced by [3-(4-morpholinyl)propyl]amine in the procedure of Example 3a and this compound processed as described in Example 3a and 3b, 1,2,3,4-tetrahydro-6-methyl-8-[[3-(4-morpholinyl)propyl]amino]-2-oxopyrido[2,3-b]pyrazine-7-carboxylic acid, ethyl ester is obtained, m.p. 168°–170° (methanol).

The following additional products are obtained by the procedure of Example 1 by appropriate substitution for the 4,6-dihydroxy-2-methyl-5-nitropyridine-3-carboxylic acid ester in part *a* and/or substitution for the butylamine in part *b*:

| Example | R | $R^1$ | $R^2$ |
|---------|---|-------|-------|
| 6 | H | $C_4H_9$ | H |
| 7 | $C_2H_5$ | H | $CH_3$ |
| 8 | $C_2H_5$ | $C_2H_5$ | $CH_3$ |
| 9 | $C_2H_5$ | $C_3H_7$ | H |
| 10 | $C_2H_5$ | $CH_3$ | $C_2H_5$ |
| 11 | H | –C₆H₅ | H |
| 12 | $C_2H_5$ | –C₆H₄–CF₃ | $CH_3$ |
| 13 | H | –C₆H₄–COOH | H |
| 14 | $CH_3$ | –C₆H₄–CH₃ | H |
| 15 | $C_2H_5$ | –C₆H₅ | H |

-continued

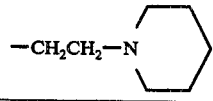

| Example | R | R¹ | R² |
|---|---|---|---|
| 16 | $C_2H_5$ | (2,5-dimethylphenyl) | $CH_3$ |
| 17 | $C_2H_5$ | (phenyl) | $CH_3$ |
| 18 | $C_2H_5$ | (3,4-dimethoxyphenyl) | H |
| 19 | $C_2H_5$ | (4-chlorophenyl) | H |
| 20 | $CH_3$ | (2,4-dibromophenyl) | H |
| 21 | H | (4-aminophenyl) | H |
| 22 | $C_3H_7$ | $-CH_2CH_2N(C_2H_5)_2$ | $C_2H_5$ |
| 23 | H | $-CH_2CH_2N(CH_3)_2$ | H |
| 24 | H | $-CH_3$ | H |
| 25 | H | (4-methylphenyl) | $CH_3$ |
| 26 | $C_2H_5$ | (phenyl) | H |
| 27 | H | $-(CH_2)_3N(C_2H_5)_2$ | H |
| 28 | $C_2H_5$ | $-C_4H_9$ | $C_4H_9$ |
| 29 | $C_2H_5$ | $-C_4H_9$ | H |
| 30 | $C_4H_9$ | $-CH_3$ | $CH_3$ |

-continued

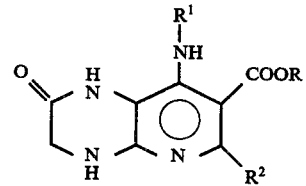

| Example | R | R¹ | R² |
|---|---|---|---|
| 31 | H | H | H |
| 32 | $C_2H_5$ | H | $CH_3$ |
| 33 | $C_2H_5$ | H | H |
| 34 | H | $-CH_2CH_2-N(\text{thiomorpholino})$ | $CH_3$ |
| 35 | $C_2H_5$ | $-(CH_2)_3-N(\text{piperazino-NH})$ | $CH_3$ |
| 36 | H | $-(CH_2)_3-N(\text{piperazino-NH})$ | $CH_3$ |
| 37 | $C_2H_5$ | $-(CH_2)_3-N(\text{piperidino})$ | H |
| 38 | H | $-CH_2CH_2-N(\text{piperidino})$ | H |

What is claimed is:

1. A compound of the formula

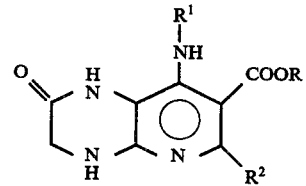

wherein R and R² each is hydrogen or lower alkyl; R¹ is morpholino-lower alkylene, thiamorpholino-lower alkylene, piperazino-lower alkylene or piperidino-lower alkylene; and physiologically acceptable acid addition salts thereof.

2. A compound as in claim 1 wherein R is hydrogen or lower alkyl or 1 to 4 carbon atoms; R¹ is morpholino-lower alkylene; and R² is lower alkyl.

3. A compound as in claim 1 wherein R and R² is lower alkyl.

4. A compound as in claim 1 wherein R is ethyl; R² is methyl; and R¹ is morpholino-lower alkylene.

5. A compound as in claim 1 wherein R is ethyl, R² is methyl and R¹ is morpholinopropyl.

* * * * *